United States Patent [19]

Potts

[11] Patent Number: 4,772,296
[45] Date of Patent: Sep. 20, 1988

[54] METHOD OF PURIFYING AND DEPOSITING GROUP IIIA AND GROUP VA COMPOUNDS TO PRODUCE EPITAXIAL FILMS

[75] Inventor: Thomas M. Potts, Joplin, Mo.

[73] Assignee: Eagle-Picher Industries, Inc., Cincinnati, Ohio

[21] Appl. No.: 49,590

[22] Filed: May 12, 1987

[51] Int. Cl.$^4$ .............................................. B01D 15/08
[52] U.S. Cl. .......................................... 55/67; 55/72; 423/87; 423/130
[58] Field of Search ......................... 55/67, 72, 74, 75; 423/87, 111, 130, 347, 349, 645

[56] References Cited

U.S. PATENT DOCUMENTS

| | | | |
|---|---|---|---|
| 3,019,087 | 1/1962 | Jacob et al. | 423/347 X |
| 3,041,141 | 6/1962 | Shoemaker et al. | 423/347 |
| 4,070,444 | 1/1978 | Ingle | 423/349 |
| 4,159,966 | 7/1979 | Roberts | 55/67 X |
| 4,532,120 | 7/1985 | Smith et al. | 423/347 |
| 4,537,759 | 8/1985 | Walker et al. | 423/349 |

FOREIGN PATENT DOCUMENTS

| | | | |
|---|---|---|---|
| 2139155 | 2/1973 | Fed. Rep. of Germany | 423/347 |
| 36203 | 11/1970 | Japan | 423/87 |
| 54298 | 5/1974 | Japan | 423/347 |
| 30711 | 2/1984 | Japan | 423/347 |

Primary Examiner—Robert Spitzer
Attorney, Agent, or Firm—Wood, Herron & Evans

[57] ABSTRACT

Thermally decomposable Group IIIa compounds are purified by conveying the relatively impure material through a prescrubber module, then heating the scrubbed Group IIIa compound and conveying same through a preconditioned gas chromatographic column packed with a porous polymeric material. After isolation, the purified material is cooled, demisted amd collected. Thermally decomposable Group Va compounds are purified by conveying the heated relatively impure material through a preconditioned gas chromatographic column packed with a porous polymeric material. After isolation, the purified material is cooled and collected. Epitaxial semiconductor films of purified thermally decomposable Group IIIa and Group Va compounds with added dopant are prepared by diluting the film components with inert carrier gas to predetermined concentration levels, thoroughly mixing the components, then depositing a crystal layer prepared from the mixed components onto a substrate by thermally decomposing the mixed components in a reactor.

7 Claims, 2 Drawing Sheets

METHOD OF PURIFYING AND DEPOSITING GROUP IIIA AND GROUP VA COMPOUNDS TO PRODUCE EPITAXIAL FILMS

BACKGROUND OF THE INVENTION

The presence of unwanted impurities in a semiconductor material can have drastic results on the conductive properties of the semiconductor, even where such impurities are present at extremely low concentration levels. Because the unwanted impurities must in many instances be no greater than a few parts per billion, the techniques employed to purify the starting materials must be extremely rigorous to achieve the exacting standards imposed.

Various techniques have been developed wherein an impure starting material is treated to remove very high percentages of undesirable impurities mixed therewith. For example, starting materials can be subjected to cryogenic distillation or pressure distillation, or gaseous diffusion, or solid phase zone refining. However, in those techniques, as well as with other available purification methods, the level of purity which must be consistently maintained to produce semiconductor-grade material in large quantity either cannot be reached at all or can be attained only at a prohibitive cost.

After the starting material has been purified to semiconductor-grade standards, it still must be further processed to produce a conductive semiconductor film having acceptable physical and electronic properties. Where the semiconductor is produced from a single material such as silicon, combined with a dopant, the manufacturing process is less complex than that wherein two or more materials are combined in conjunction with dopant to produce a binary, ternary or higher semiconductor film.

Semiconductors are produced by the successive build-up of individual layers of semiconductor-grade material and dopant. To derive reproducible electronic characteristics from a silicon film, it is necessary for the silicon film manufacturer to introduce a precise amount of uniformly dispersed electronically-active dopant. The resulting film should appear under high magnification as a uniform plane of silicon with interspersed dopant material. The presence of impurities in the film interrupts the planar uniformity and results in stress points which can alter both the structural and electronic integrity of the film. It can be appreciated that a film comprised of two, three, or more components of different atomic geometries in addition to a dopant will be more susceptible to structural and electronic defects than a silicon film unless the components, essentially free of adulterants, are uniformly combined in precise ratios. It is also highly desired that the deposited layer of semiconductor-grade material and dopant be unaffected by the deposition of additional layers. Where deposition occurs by thermal decomposition, the dopant in the underlying layers may diffuse from one layer to another or may migrate within a single layer if the temperature of deposition is too high. High temperatures are necessary to deposit semiconductor materials which are resistant to decomposition, i.e., stable. It is preferred that the semiconductor material be relatively unstable, to facilitate decomposition; however, such materials are difficult to purify because of their instability. Ideally, such relatively unstable semiconductor materials would be purifiable under moderate conditions which remove undesired components and permit thermally-induced deposition at temperatures which do not result in dopant diffusion or migration.

Silicon has long been used in the manufacture of semiconductors. However, other materials may be employed to manufacture semiconductors, and in certain instances these materials possess electronic characteristics superior to those of silicon. A silicon atom has four valence electrons; in a lattice of silicon atoms, the overwhelming majority of valence electrons act as a "glue" to bond the crystal lattice together. Because very few of the silicon valence electrons are available to conduct current, the silicon lattice is a relatively poor conductor without the addition of another material (a dopant) which fits into the lattice and has either an excess or a shortage of electrons to facilitate passage of either negative or positive current. Combinations of elements such as gallium and arsenic or aluminum, gallium and arsenic may also be used to manufacture a crystal lattice to form a semiconductor. Gallium and aluminum are Group IIIa elements which have three valence electrons while arsenic is a Group Va element which has five valence electrons. A crystal lattice of gallium arsenide has the same number of available valence electrons as a silicon crystal. However, because of its different atomic properties, a gallium arsenide crystal causes the conduction electrons to move at a much higher velocity than that of silicon electrons. In gallium arsenide the maximum electron velocity is about $10^8$ centimeters per second, while in silicon the maximum velocity is about $2 \times 10^7$ centimeters per second. Conduction electrons in an aluminum gallium arsenide crystal travel even faster than those in the gallium arsenide crystal. Additionally, electrons in the gallium arsenide crystal are less likely to collide with the lattice than is the case in a silicon crystal. The mean free path of an electron in moderately doped gallium arsenide is roughly ten times the mean free path of electrons in silicon. M. Heiblum, L. Eastman, "Ballistic Electrons in Semiconductors", *Scientific American*, 256, No. 2, p. 102 (1987).

Where the semiconductor film comprises two or more components, the need for the purification procedure to deliver a product having reproducible, low levels of impurities is more pronounced. Typically, the semiconductor film manufacturer purchasing already-purified starting materials will encounter substantial lot-to-lot variation in the actual level of impurities in the material as delivered. Such variation has marked effects on the conductivity of the resulting epitaxial film. In addition, the purification processes used by individual suppliers employing standard distillation and refining techniques have limitations as to the removal of certain impurities, such as materials which azeotrope with the desired starting material, compounds with very similar boiling points and organic compounds.

It is an object of this invention to provide a method whereby relatively impure, relatively unstable starting materials containing Group IIIa and Group Va elements are purified such that residual impurities consistently do not exceed parts per billion levels.

It is a further object of this invention to provide a process for the production of consistently high quality films by thermal decomposition from a variety of starting materials for use in semiconductor devices whereby dopant diffusion and migration are minimized.

Further objects and attendant advantages of the present invention will become better understood from the following description.

BRIEF DESCRIPTION OF THE INVENTION

The invention is directed toward the preparation of two, three or more component semiconductor films derived from purified semiconductor-grade materials. After an initial purification step by gas chromatography, the individual purified materials in the gaseous phase are diluted in the same or different proportions using an inert gas. Either before or after combination of the diluted, purified gases, a gaseous phase dopant not exceeding 10 ppm concentration is added. After combination of the diluted gases and the dopant, a film is produced by thermally decomposing the combined gases on the surface of a substrate.

The starting materials used to produce epitaxial films for semiconductor and optoelectronic device applications as envisioned herein are compounds produced from elements in Group IIIa and Group Va of the Periodic Table. Specifically, such compounds include the halides, hydrides, mixed halohydrides, and alkyl and aryl compounds of one to twelve carbon atoms of nitrogen, phosphorus, arsenic, antimony, bismuth, boron, aluminum, gallium, indium and thallium. Examples of these compounds include trimethylgallium ($Ga(CH_3)_3$), phosphine ($PH_3$), arsine ($AsH_3$), arsenic trichloride ($AsCl_3$), triphenylaluminum ($Al(C_6H_5)_3$), dimethylarsine ($(CH_3)_2AsH$), triethylbismuth ($Bi(C_2H_5)_3$), and indium tribromide ($InBr_3$).

The starting materials used in carrying out the process of this reaction may contain a relatively large amount of impurities when compared to the purified form of the same materials. Such relatively impure starting materials are commercially available.

The purification of the compounds containing Group Va elements proceeds by introducing the impure compound into a gas chromatograph inlet port in a series of timed pulses. Each pulse is carried through the gas chromatograph column by means of a constant flow of inert carrier gas, such as hydrogen.

The packing in the gas chromatograph column is preferably composed of a porous polymer packing material. A molecular sieve-type packing may also be used, but it does not exhibit the same repeatability of results obtained with the porous polymer packing, nor does it resist degradation as long as the polymer packing.

The specific packing material utilized is important to the practice of this invention. Further, in a preferred form of the invention, it has been found that the separation efficiency of the column can be further improved by subjecting the packing in the column initially to heat and subsequently to an undiluted stream of the material to be purified, prior to use as a separation column. This preconditioning step should be conducted at a temperature in the range of 10° to 30° C. below the maximum operating temperature of the packed column. Heat is applied to the packed column for approximately one hour. The heat is then removed and the undiluted stream of material is passed through the packed column for about thirty minutes.

During the purification operation of the gas chromatograph, relatively impure starting material is introduced into the inlet of the separation column using a timed valving device which periodically opens to permit flow of the starting material through the column. The starting material is mixed with a constant flow of inert carrier gas at the inlet port. This pulse of starting material is carried into the column by the flow of inert gas. As the pulse progresses through the column, the impurities begin to separate from the desired fraction due to the different retention times on the column packing material. By the time the initial pulse reaches the end of the column, the impurities have separated from the desired fraction to an extent sufficient to permit recapture of the desired fraction substantially free of all impurities by directing the desired fraction to a receiver through the use of a discriminating device operating in concert with a detector or a timer.

As the pulse containing the desired fraction mixed with inert carrier gas travels through the packed column, the retention and release properties of the packing material cause the pulse to increase in length within the column. This "lengthening" process ultimately permits the separation of a desired fraction from impurities. However, it also increases the time window through which the desired fraction elutes from the column. The desired fraction does not elute at a constant concentration; the plot of concentration in carrier gas versus time approximates a Gaussian curve. A valving device connected to a detector or timing device permits segregation of the eluting desired fraction from the impurities such that the collection window encompassing the desired fraction may be increased to obtain maximum product, or decreased to obtain maximum purity.

Because of the peak broadening phenomenon which occurs in the packed column, the concentration of desired fraction in inert carrier gas varies at the column outlet and consequently also in the receiver. For the purpose of producing a high quality epitaxial film using the desired fraction from this purification process as a component thereof, a specific concentration of desired fraction to carrier gas is required. A sensor is used to measure the concentration of the desired fraction in carrier gas, the sensor being connected to a valve which opens to add carrier gas to the column outlet gas flow should the desired fraction concentration level become too high. The system parameters are set such that the desired fraction concentration will not be too low in the receiver.

Several of the Group Va compounds designated for use in this invention are generally classified as strong irritants and poisons. Therefore, extreme care must be taken in avoiding or minimizing human exposure to these compounds. To this end, a variety of safety devices are integral to the overall system through which the Group Va compounds flow. Among these are leak detectors, overpressure sensors, overtemperature sensors, and unexpected detector response sensors.

The Group IIIa compounds are purified in much the same way as the Group Va compounds. At column temperatures approaching maximum separation efficiency, however, the Group IIIa compounds tend to decompose. To maintain compositional integrity, the column temperature is decreased. However, in decreasing the column temperature, the separation efficiency also decreases. A prescrubber is provided prior to the column inlet; this aids in purification. In addition, when the desired Group IIIa fraction exits the column outlet, it tends to be in the form of a mist which hampers the collection process. A demisting device is provided to improve collection of the desired Group IIIa fraction after the fraction exits the column outlet. After demisting, the desired Group IIIa fraction is directed to a receiver.

In production of the epitaxial film, the ratio of the purified Group Va compound to the purified Group IIIa compound must remain constant to ensure the proper crystal growth on the substrate. Material flow from the individual receivers containing purified Group IIIa and Group Va compounds is regulated by various metering devices. Dopant is added to the combination of purified Group IIIa and Group Va compounds at a mixing manifold. The dopant and purified Group IIIa and Group Va compounds are then introduced into a reactor wherein the materials are thermally decomposed on a substrate to form the film.

THE PRIOR ART

Silicon-containing compounds have been purified using techniques taught in Jacob et al U.S. Pat. No. 3,019,087, and in Shoemaker et al U.S. Pat. No. 3,041,141.

The production of Group IVa elemental silicon from impure silane feed is taught in Walker et al U.S. Pat. No. 4,537,759. The Walker patent describes a process wherein $SiH_4$ gas is separated from impurities in the gas by passing the $SiH_4$ feed through a large scale gas chromatographic column and selectively removing pure $SiH_4$ from those impurities which elute at different times from the chromatographic column. However, Walker deals only with the purification of inorganic silane, a Group IVa hydride compound which is gaseous at room temperature. Walker does not address the purification of non-$SiH_4$ materials, the purification of materials which are liquid at room temperature, the combination of multiple purified components, the purification of relatively unstable materials, or the eventual final use of the purified components.

The inventors believe that the purification of phosphine ($PH_3$) may have been attempted using gas chromatography in the 1950's by a company known as Abcor. However, it is not known whether this attempt by Abcor met with any success.

Until now, no method has been known which can purify commercial quantities of both liquid and gaseous Group IIIa and Va compounds to the degree necessary for use in semiconductor applications. Nor until now has it been known to produce consistently high quality two, three, or more component epitaxial films at a manufacturing cost comparable to that for producing single component films.

DESCRIPTION OF THE DRAWINGS

The invention can be further disclosed by referring to the accompanying drawings, in which.

DETAILED DESCRIPTION

Thermally decomposable Group IIIa and Group Va compounds are first purified, then combined in the presence of a dopant and thermally decomposed onto a substrate to form a conductive film. Unless otherwise specified, all components of the purification and deposition systems are leak-free and chemically inert to the presence of the Group IIIa and Group Va compounds, the impurities included therewith, the dopants and the carrier gas. Typically, Grade 316L stainless steel is utilized in constructing the purification and deposition system components which contact the film components or the impurities thereof.

Figure 1:
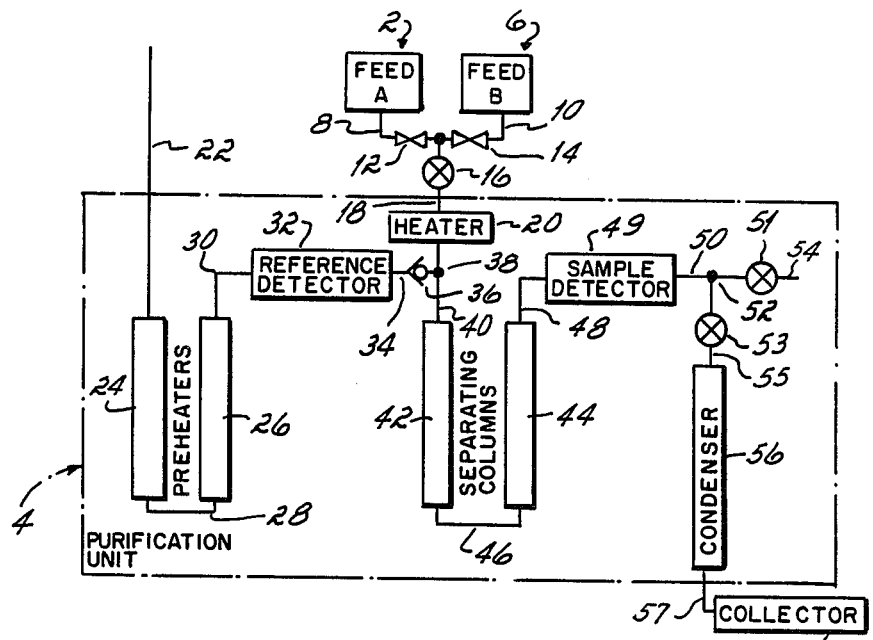
FIG. 1 is a flow diagram of a Group Va material purification unit in accordance with a preferred embodiment of the invention.

Halides, hydrides, mixed halohydrides, and alkyl and aryl compounds having from one to twelve carbon atoms of the Group Va elements nitrogen, phosphorus, arsenic, antimony and bismuth are purified to semiconductor-grade standards by the process as shown diagrammatically in FIG. 1.

Relatively impure Group Va compound feed material is located in feed source 2. Typically, the starting material is approximately 99.9% pure, though material having different levels of impurities may also be processed. Depending on the composition of the compound, the feed may be in either the liquid or gaseous state. To assure a constant supply of impure feed for the gas chromatograph purification unit 4, one or more redundant feed sources 6 may be connected into the purification unit 4. Feed from source 2 flows through feed line 8. Feed from redundant feed source 6 flows through feed line 10. Flows from the feed sources 2 and 6 are regulated by valves 12 and 14, respectively.

The impure feed flows to automatic valve 16 which opens and closes by automatically-operated signal to cause the impure feed to flow into the gas chromatograph purification unit 4 as a series of pulses. The rate typically falls in the range of 6 to 30 pulses per hour. The pulse of impure feed flows through purification unit inlet line 18 to heater 20. The heater brings the impure feed to a temperature approximately 10° to 12° C. higher than that of the separating columns, described below. If the impure feed is in the liquid state, the heater provides the additional function of vaporizing the liquid. The heater ensures that no temperature gradient will be established at the front of the separating column; such a gradient would adversely affect the column's separating characteristics. Heater 20 increases the temperature of the impure feed to approximately match that of the carrier gas which will carry or sweep the impure feed through the gas chromatograph purification unit 4.

The carrier gas is fed into the purification unit 4 by means of gas inlet line 22. The carrier gas is inert to the materials comprising the feedstock, and may be nitrogen, hydrogen, helium, argon or other material. The carrier gas flows through line 22 to preheaters 24 and 26 joined by connector line 28. The preheaters 24 and 26 increase the temperature of the carrier gas to approximately match that of the impure feed as it exits the heater 20. The preheaters are lined with stainless steel mesh to increase surface area and improve heat transfer. The preheaters 24 and 26 may be heated by the same source as is used to heat the separating columns. Alternatively, individual heat sources may be affixed to the preheaters to permit individual control.

The carrier gas exits preheater 26 and flows through detector input line 30 to reference detector 32. Reference detector 32 is typically a thermal conductivity device but may be of different construction. The reference detector 32 serves to produce a reference signal which functions as a base line upon which any signal attributable to sample will be superimposed.

The carrier gas exits reference detector 32, flows through line 34 and check valve 36 and mixes with heated impure feed at line junction 38. Check valve 36 is interposed between junction 38 and detector 32 to prevent flow of impure feed into the reference detector. The carrier gas flows through column input line 40 along with a concentrated pulse or "plug" of heated impure feed to separating columns 42 and 44 joined by connector line 46. In the preferred method of practicing the invention, columns 42 and 44 are packed with porous polymer such as "Poropak" material from Waters Associates of Milford, Mass. or "Chromosorb Century" material from Mansville Corp. and operate at a temperature in the range of approximately 90° to 200° C. The packed columns are preconditioned at a temperature of about 180° to 220° C. for approximately one hour. The columns then accept a stream of undiluted impure feed for at least 30 minutes. The columns are then ready for separation use.

The composition of the gas in the column input line 40 at the time the gas flows into column 42 will vary because of the pulsing effect of automatic valve 16. When the automatic valve 16 is closed, undiluted carrier gas flows through line junction 38 and along column input line 40. When the automatic valve 16 opens, a heated pulse or "plug" of essentially undiluted gaseous impure feed flows past line junction 38 along column input line 40 shortly thereafter. Feed line pressure above the point where impure feed and carrier gas meet at line junction 38 is maintained at a higher value than the pressure in the carrier gas line 34 before the junction 38, in order to minimize carrier gas backflow into the feed source 2 or 6.

Carrier gas interrupted with discrete pulses of impure gaseous feed flows into separating columns 42 and 44 joined by connector line 46. The carrier gas is minimally hindered by the porous polymer packing in the columns and continues its forward flow. Components in the gaseous impure feed, however, interact with the column packing to different degrees. Some impurities may interact with the packing to a lesser degree than the desired material and will exit column 44 before the desired material. Some impurities may interact with the packing to a higher degree and will exit column 44 after the desired material. The flow rate, pulse rate and column temperature are adjusted so that the maximum volume of desired material having the requisite purity is obtained, using techniques which are known per se.

The carrier gas-impure feed composite mixture exits column 44 through detector input line 48 into sample detector 49. The detector again is typically a thermal conductivity device. The presence and concentration of impure feed components are determined by measuring the thermal conductivity of the gas mixture as it flows through sample detector 49. The signal produced by the sample detector 49 is compared electronically with the signal from the reference detector 32. A comparator circuit (not shown) factors out the signal contribution due to the carrier gas to produce a net signal corresponding only to the components of the impure feed.

The separated gaseous impurities are vented or diverted from the system by means of automatic valves 51 and 53. As the gas composite mixture exits sample detector 49 it flows through detector outlet line 50. Automatic valves 51 and 53 are actuated either by a signal from sample detector 49 or by a timer (not shown). When gaseous impurities combined with carrier gas reach line junction 52, automatic valve 51 opens and automatic valve 53 closes, causing the gaseous impurities with carrier gas to be vented or diverted from the system via vent line 54. After the gaseous impurities with carrier gas have passed through automatic valve 51, automatic valve 51 closes and automatic valve 53 opens. Desired material with carrier gas then flows along condenser inlet line 55 and enters condenser 56. Condenser 56 is typically nitrogen cooled, and is adjusted so as to condense only desired material to the liquid state. After the purified desired material has been liquified, it is directed along condenser outlet line 57 to a suitable collector and/or storage unit 58. The purity of the desired material in the collector/storage unit is greater than 99.9999% pure. Carrier gas subsequent to condensation of the desired material is vented through a scrubber apparatus (not shown).

Figure 2:
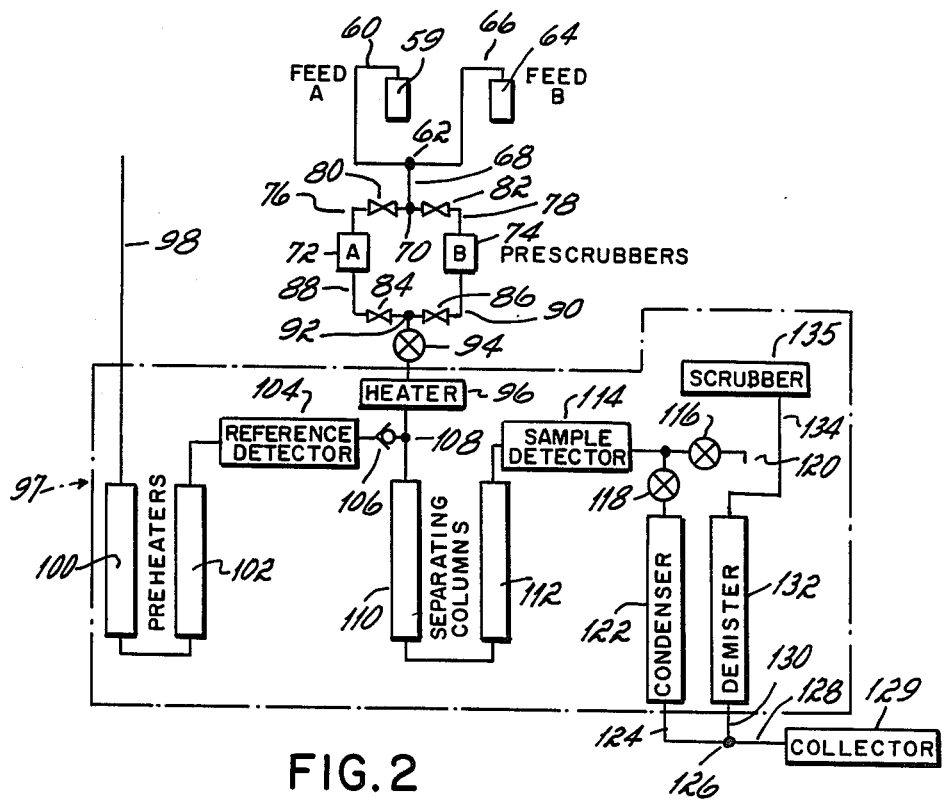
FIG. 2 is a flow diagram of a preferred embodiment of a Group IIIa material purification unit.

Halides, hydrides, mixed halohydrides, and alkyl and aryl compounds having from one to twelve carbon atoms of the Group IIIa elements boron, aluminum, gallium, indium, and thallium are purified to semiconductor-grade standards by the process as outlined in FIG. 2.

Relatively impure Group IIIa compound feed material at approximately 99.9% purity from feed source 59 flows through source outlet line 60 to line junction 62. To maintain a constant supply of impure feed, one or more redundant feed sources 64 can be installed. Feed from redundant source 64 would flow through source outlet line 66 to line junction 62.

Impure feed then flows through connector line 68 to prescrubber inlet junction 70. The feed can then be directed to either one of two identical prescrubbers 72 or 74 through prescrubber inlet lines 76 or 78. The prescrubbers have been found very useful because the Group IIIa compounds used in semiconductor manufacture applications are difficult to purify. Group IIIa compounds are less stable and therefore more easily thermally decomposed than Group Va compounds. As a result, less vigorous gas chromatographic purification techniques must be used, which has the overall effect of decreasing separation efficiency. The prescrubbers function to remove some of the impurities from the feed while still at ambient temperature. The prescrubbers 72 and 74 remove impurities by means of a bed of molecular sieve material or activated carbon through which the impure feed flows. When the removal efficiency of one prescrubber decreases as a result of an excessive amount of impurities retained on the molecular sieve material or activated carbon, the impure feed is redirected to the other prescrubber by adjusting valves 80, 82, 84 and 86 while the bed in the first prescrubber is regenerated. This switching capability permits uninterrupted flow of the impure feed through the prescrubbers.

After treatment in either prescrubber 72 or 74, the feed flows through prescrubber outlet lines 88 or 90, respectively, to prescrubber outlet junction 92. The feed then flows to automatic valve 94 which pulses feed at a rate of typically 6 to 30 pulses per hour into heater 96 of gas chromatograph purification unit 97 in a manner similar to that described in purifying Group Va compounds in FIG. 1.

As previously described for the Group Va purification process, inert carrier gas such as nitrogen, hydrogen, helium, argon or other material flows through gas inlet line 98 and is heated to approximately the same temperature as that of the feed as the feed exits the heater 96. Heating of the carrier gas is accomplished by preheaters 100 and 102. The heated carrier gas flows through reference detector 104, past check valve 106 to line junction 108. The carrier gas then flows together with discrete pulses of feed through separating columns 110 and 112, and through sample detector 114. Impurities are vented or diverted from the system using automatic valves 116 and 118 working in opposition connected to a timer or actuated by a signal from sample detector 114. The vented or diverted gases flow through vent line 120.

In condenser 122, the now-purified Group IIIa compound is cooled to form the liquid state. However, the purified gas does not easily convert to the liquid state. The Group IIIa compounds on cooling tend to form an aerosol in the gas phase instead of condensing on the inside walls of condenser 122. To collect the purified material in aerosol form, the carrier gas with the aerosol flows through condenser outlet line 124 along with purified liquid Group IIIa compound to outlet junction 126. The purified liquid flows through outlet line 128 to a suitable collector and/or storage unit 129 which may be conventional. Carrier gas with purified material in aerosol form flows along connector line 130 to demister 132. The demister is packed with stainless steel mesh to provide a large surface area upon which the purified material in aerosol form can convert to the liquid state. Liquid purified material then flows back through connector 130, past outlet junction 126 and through outlet line 128 to a suitable collector and/or storage unit 129 which may be conventional. Carrier gas and residual unconverted aerosol flow through vent line 134 to a scrubber 135 which also may be conven- tional.

Purified Group IIIa and Group Va compounds may then be shipped off-site in suitable containers to film manufacturers, or they may be used on-site to directly manufacture epitaxial film for semiconductors.

Broadly, the manufacture of an epitaxial film by thermal decomposition requires the transfer of a specified amount of one or more purified Group IIIa and Group Va compounds to a mixing manifold, along with a specified amount of one or more dopants and carrier gas. The individual components are then thoroughly mixed so that the gaseous blend is homogeneous. The homogeneous blend flows to a thermal decomposition reactor which houses a substrate upon which the homogeneous blend minus the carrier gas deposits as a solid under the action of heat.

Figure 3:
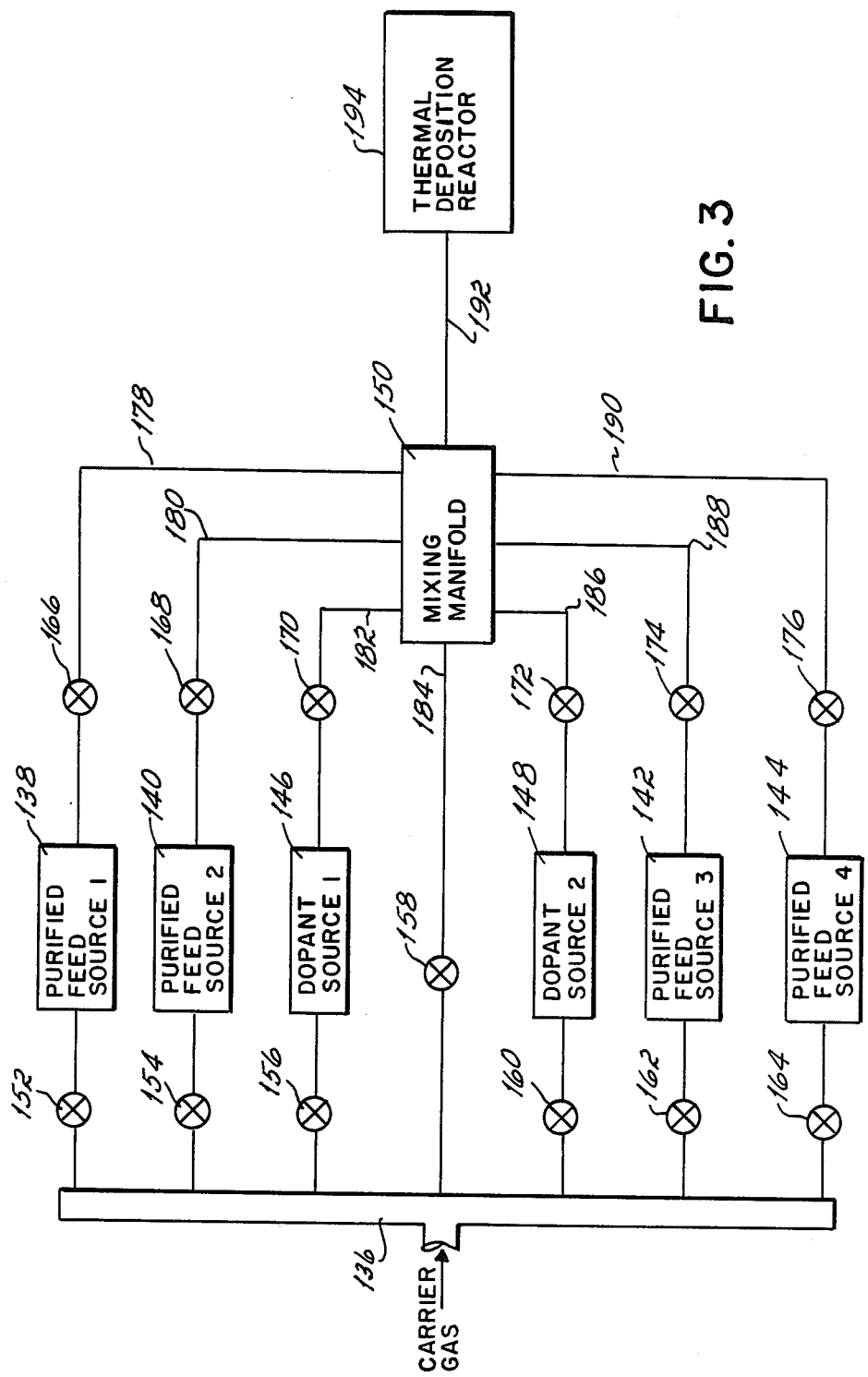
FIG. 3 is a flow diagram of the final mixing stage of the purified components which precedes the thermal deposition onto a substrate.

In FIG. 3, carrier gas flows into a manifold 136, then to purified feed sources 138, 140, 142, and 144. Carrier gas can also be supplied to dopant sources 146 and 148. Carrier gas can also be supplied directly to the mixing manifold 150. Carrier gas flow to the purified feed sources, dopant sources and mixing manifold is regulated by valves 152, 154, 156, 158, 160, 162 and 164.

Films of the type here involved often have one Group IIIa compound component, one Group Va compound component, and a single dopant. The system as presented in FIG. 3 for illustrative purposes permits the utilization of up to four discrete feed materials and two dopants. Films may be prepared according to the teachings of this invention which have more components than could be accommodated by the system of FIG. 3.

Carrier gas may be transferred to the mixing manifold 150 directly; it may enter the mixing manifold 150 in combination with either one or more of the purified feeds or dopants; or it may enter the mixing manifold 150 by means of a combination of the two operations. Likewise, the feed sources and dopants may enter the mixing manifolds 150 in undiluted form or as a mixture with carrier gas. The flow of purified sources 138, 140, 142 and 144 and dopants 146 and 148 with or without carrier gas are regulated by regulator valves 166, 168, 170, 172, 174 and 176.

Typically, Group IIIa compounds are combined with carrier gas at the purified feed source, the compound arriving at the mixing manifold 150 in diluted form. Group Va compounds typically enter the mixing manifold 150 without prior dilution. Dopant may enter the manifold in either diluted or undiluted form. The above methods are typical, not exclusive. Group IIIa compounds may enter the mixing manifold undiluted, as likewise the Group Va compounds may be premixed with carrier gas.

After the components in specified amounts enter mixing manifold 150 via inlet lines 178, 180, 182, 184, 186, 188 and 190, the components are thoroughly combined. The means of combining the components via the manifold is proprietary to the manifold manufacturer, but it generally consists of a complex array of baffles and valves to facilitate intimate mixing. Such manifolds are available from CVD Equipment, Deer Park, N.Y., Emcore, South Plainfield, N.J., Spire, New Bedford, Mass., and Semacs, Phoenix, Ariz.

The thoroughly mixed blend of components then flows through reactor inlet line 192 to thermal deposition reactor 194. Deposition of the homogeneous mixture onto a substrate occurs upon proper control of the gaseous blend feed rate and of the conditions for pyrolyzing the gaseous blend. For example, in the manufacture of a gallium arsenide (GaAs) film, a mixture of arsine ($AsH_3$), trimethylgallium (($CH_3)_3Ga$) and diethylzinc (($CH_3CH_2)_2Zn$) dopant are conducted into a chemical vapor deposition reactor by means of hydrogen carrier gas. The ratio of arsine to trimethylgallium is about 13 to 1, which is necessary to compensate for the large amount of arsine lost before the deposition is completed. For every mole of trimethylgallium, approximately $2 \times 10^{-7}$ mole diethylzinc is added as dopant. The concentration of arsine in carrier gas near the substrate is 2.5 to 3.0%. Trimethylgallium is present at the level of 0.20 to 023%. The gaseous mixture of arsine, trimethylgallium, diethylzinc and hydrogen flows past one or more gas-deflecting baffles to provide for a smooth, uninterrupted flow over the substrate, which is typically a thin plate having a uniform thickness from 2 to 5 mm and composed of gallium arsenide. The gas mixture flow rate is less than 20 cm/sec. Deposition of gallium, arsenic and zinc is accomplished by the generation of heat from radio frequency induction source resistance heaters or even from a high-power lamp. The heat source is directed onto the substrate, over which surface the gas mixture flows. At substrate surface temperatures of about 500° to about 800° C., the gas mixture components (except for hydrogen) decompose, releasing hydrogen, methyl and ethyl ions which recombine to form a variety of gaseous organic molecules which are vented from the reactor with the hydrogen carrier gas. The surface of the substrate after decomposition is comprised of a uniform crystalline layer of gallium and arsenic atoms with zinc homogeneously dispersed throughout at a concentration of approximately one part per million. Epitaxial films can be produced having thicknesses ranging from 0.1 to 20 microns.

A conductive epitaxial film is comprised of a number of individual layers of deposited material. Films may be built up of as many as 500 layers of deposited material, or even more. Films which have optimum reproducible electronic characteristics are built up of layers of homogeneously deposited components which do not migrate after deposition.

Earlier efforts at preparing conductive films of Group IIIa and Group Va elements such as GaAs were limited to using relatively stable precursor compounds, which were required to withstand the vigorous purification procedure needed to bring the compounds to semiconductor-grade purity. Consequently, large amounts of heat input were needed to cause the decomposition and layer deposition of the precursor components. The high temperatures needed to decompose the precursor compounds tended to cause atomic-level changes in the already-deposited crystal layers. Dopant atoms tended to diffuse from one layer to another, or to migrate within a single layer.

According to the teachings of this invention, Group IIIa and Group Va compounds which are relatively less stable may be purified for eventual use as a component of an epitaxial film. The use of less stable precursors permits the deposition by thermal decomposition to be conducted at lower temperatures. Lower temperature deposition decreases the tendency of components in already-deposited layers from migrating or from cross-diffusing from one layer to another. Therefore, film inhomogeneity is minimized and superior electronic characteristics result. By proper control of the gas flow and thermal conditions, very sophisticated films can be produced having individual layers only about 20 angstroms in thickness. Investigations to date indicate that room temperature mobilities of undoped films are increased by about 70% over those of films grown from material purified by conventional techniques.

Having described this invention and its operating parameters, variations may be achieved without departing from the spirit and scope hereof.

We claim:

1. A method of purifying thermally decomposable Group IIIa and Group Va compounds of the formula $MR_3$, wherein M is a Group IIIa or Group Va element and R is selected from one or more of the group consisting of hydrogen, halogen, and aliphatic and aromatic organic moieties having from one or twelve carbon atoms, said method comprising:

passing an impure feed, in the gaseous phase and containing the Group IIIa or Group Va compound and undesirable impurities, through a gas chromatograph having a packing which differentiates the flow through it of said Group IIIa or Group Va compound from said impurities, said feed being injected into said chromatograph as a series of regularly spaced pulses in a continuous stream of an inert carrier gas;

said column differentially separating the Group IIIa or Group Va compound in each respective pulse from the impurities therein so that said Group IIIa or Group Va compound elutes from the column at a different time than said impurities; and directing the eluted Group IIIa or Group Va compound component of each respective pulse to a receiver separately from the impurity components of each pulse.

2. The improvement of claim 1 further wherein said feed contains a Group IIIa compound and is passed through a prescrubber of activated carbon, prior to introduction into said gas chromatograph.

3. The improvement of claim 1 wherein said feed contains said Group IIIa compound, and further wherein said compound after elution from said gas chromatograph is passed through a condenser and a demister.

4. The improvement of claim 1 further wherein the gas chromatograph column used in individually purifying both Group IIIa and Group Va compounds has a packing selected from the group consisting of porous polymer and molecular sieve column packing materials.

5. The improvement of claim 1 further wherein said column is preconditioned by heating the column and packing therein for a period of at least one hour at a temperature about 10° to about 30° C. below the maximum operating temperature of the packing, then flowing a stream of Group IIIa or Group Va compound gas over the packing and heating for a period of at least about one-half hour.

6. The improvement of claim 1 further wherein said Group IIIa compound is trimethylgallium.

7. The improvement of claim 1 further wherein said Group Va compound is arsine.

* * * * *

UNITED STATES PATENT AND TRADEMARK OFFICE
CERTIFICATE OF CORRECTION

PATENT NO. : 4,772,296
DATED : September 20, 1988
INVENTOR(S) : Thomas M. Potts

It is certified that error appears in the above-identified patent and that said Letters Patent is hereby corrected as shown below:

Column 10, line 35, "023%" should read --0.23%--.

Signed and Sealed this

Twenty-eighth Day of November 1989

Attest:

JEFFREY M. SAMUELS

Attesting Officer     Acting Commissioner of Patents and Trademarks